United States Patent [19]

Stitt

[11] Patent Number: 5,110,592
[45] Date of Patent: May 5, 1992

[54] METHOD OF INCREASING LIVE BIRTHS TO FEMALE ANIMALS AND ANIMAL FEED BLEND SUITABLE FOR SAME

[76] Inventor: Paul A. Stitt, 123 Cleveland Ave., Manitowoc, Wis.

[21] Appl. No.: 695,071

[22] Filed: May 3, 1991

Related U.S. Application Data

[63] Continuation-in-part of Ser. No. 629,906, Dec. 19, 1990, abandoned, which is a continuation of Ser. No. 133,967, Dec. 16, 1987, abandoned.

[51] Int. Cl.$^5$ ............................................. A61K 35/78
[52] U.S. Cl. ............................ 424/195.100; 424/641; 514/552; 514/558; 426/623; 426/629; 426/630
[58] Field of Search ............................ 424/195.1, 641; 514/552, 558; 426/623, 629, 630

[56] References Cited

PUBLICATIONS

Nagdaliwa, et al., Chem. Absts. 186(15) 118599n, 1987.

Primary Examiner—John W. Rollins
Attorney, Agent, or Firm—Sughrue, Mion, Zinn, Macpeak & Seas

[57] ABSTRACT

A method for increasing the number of live births to a female animal by feeding the female animal beginning at least one week before the expected time of birth of the female animal's offspring, an edible flaxseed composition comprising ground flaxseed. This ground flaxseed composition can be admixed with a suitable animal feed. Zinc and/or vitamin B-6 can be included in the composition. An animal feed blend comprising an animal feed and a stable dry edible flaxseed composition comprising ground raw flaxseed.

61 Claims, No Drawings

# METHOD OF INCREASING LIVE BIRTHS TO FEMALE ANIMALS AND ANIMAL FEED BLEND SUITABLE FOR SAME

This is a Continuation-in-Part of pending U.S. patent application Ser. No. 07/629,906 filed on Dec. 19, 1990, now abandoned, which is a continuation of application Ser. No. 07/133,967 filed Dec. 16, 1987, now abandoned.

FIELD OF THE INVENTION

The present invention relates to a method for increasing the number of live births to a female animal by feeding the female animal beginning at least one week before the expected time of birth of the female animal's offspring, an edible flaxseed composition comprising ground flaxseed. The present invention also relates to a method for improving immune systems in animals and for allowing for earlier breeding in animals.

BACKGROUND OF THE INVENTION

Numerous attempts have been made to improve the number of live offspring produced by female animals. Low birthing rate is one of the main problems faced by animal raisers and results in millions of dollars of lost profits each year. The University of Wisconsin has reported that an increase in litter size by two piglets for a farmer that keeps 100 female swine would increase annual profits by $25,000.

While copending U.S. patent application Ser. No. 07/629,036, now U.S. Pat. No. 5,069,903, filed Dec. 19, 1990, which is a Continuation of U.S. application Ser. No. 07/133,967, filed Dec. 16, 1987, now abandoned, discloses that flaxseed contains Omega-3 Oil, as alpha-linolenic acid, and is useful for improving the health and appearance of animals, no reports are known to the present inventor of attempts to use flaxseed to increase the number of live births to a female animal or to improve animal immune systems.

U.S. Pat. No. 4,543,264 discloses a processed flaxseed-containing feed which provides growing cattle and turkey poults with an improved protein source. The flaxseed is processed by an alcohol method that removes the omega-3-containing oil from the flaxseed.

U.S. Pat. No. 3,246,989 discloses a fermented feed for calves. The fermented feed contains 20-30 percent linseed meal or extracted course-ground linseed. The object of including this fermented feed is to provide an animal feed that is less bulky and easier to handle then previously known feeds.

U.S. Pat. No. 59,255 discloses a concentrated pressed feed for stock containing a small amount of oil or flaxseed meal. Flaxseed meal is flaxseed that has been treated to remove as much Omega-3-containing oil as possible. The object is to provide a less weighty but more nutritious ration for horses and mules.

U.S. Pat. No. 4,223,011 relates to the use of long chain fatty acids as sources of prostaglandins. This patent, however, discloses the use of long chain fatty acids to control fertility, i.e., as a birth control agent.

U.S. Pat. No. 4,918,104 relates to increasing the Omega-3 in chickens and eggs from laying hens by feeding the chickens and laying hens a chicken feed comprising preformed Omega-3 or metabolic precursors thereof. The precursor can be linseed oil. There is no disclosure, however, that flaxseed can be used directly in the feed as a source of Omega-3.

SUMMARY OF THE INVENTION

Accordingly, one object of the present invention is to provide a method of increasing the number of live births to a female animal.

A second object of the present invention is to provide a method for improving the immune system of an animal.

A third object of the present invention is to provide a method for increasing the number of live births to a female animal that utilizes a compound that is abundant and has a flavor liked by animals.

A fourth object of the present invention is to provide a method for increasing the number of live births to a female animal that utilizes a compound that is not toxic to the animal, and can be administered orally.

A fifth object of the present invention is to provide a method for increasing the number of live births to a female animal that utilizes a compound that is edible and suitable for incorporation into an animal feed blend.

A sixth object of the present invention is to provide a low cost method for increasing the number of live births to a female animal that is useful in many different species of animals.

A seventh object of the present invention is to provide an animal feed blend containing raw flaxseed.

These and other objects and advantages of the present invention have been attained by providing a method for increasing the number of live births to a female animal comprising administering orally to said female animal, beginning at least one week prior to the expected time of birth of said female animal's offspring, a biologically effective amount of an edible composition comprising ground flaxseed.

In a preferred embodiment, the feeding begins by feeding the female animal's mother at least one month before the birth of the female animal and continues through the weaning of the female animal, and then feeding the female animal from weaning until the birth of one or more litters to the female animal, a biologically effective amount of an edible composition comprising ground flaxseed.

In a more preferred embodiment, the feeding begins by feeding the female animal's mother at the time of breeding or preferably one month before the time of breeding to the time of birth of the female animal and continuing through the weaning of the female animal, and then feeding the female animal from weaning until the birth of one or more litters to the female animal, a biologically effective amount of an edible composition comprising ground flaxseed.

In another preferred embodiment, the feeding begins at the time of breeding of the female animal and continues through gestation to parturition.

In another preferred embodiment, the feeding of the female animal begins one week before the expected time of birth of the offspring and continues through lactation.

In another preferred embodiment the female animal is a monogastric animal, and in an even more preferred embodiment, the female animal is a female swine.

The present invention also provides an animal feed blend comprising: (1) animal feed, and (2) a stable dry edible flaxseed composition comprising ground raw flaxseed.

DETAILED DESCRIPTION OF THE INVENTION

It appears that the oral administration of the flaxseed composition to a pregnant sow reduces the number of mummified pigs which are pigs that are not fully developed and are born dead. The method also improves perinatal survivability. These effects increase the average live weaned pigs per sow by 1 to 2 pigs per liter.

While not wanting to be bound by the following explanation, it also appears that the linolenic acid in the flaxseed improves the fertility of the animal. The linolenic acid is quickly converted in the animal into products that are major constituents of the cell walls and of the ovarian egg itself and apparently makes earlier breeding possible. Additionally, linolenic acid is a major constituent of brain cells, nerve cells, and of the retina. Linolenic acid can inhibit the conversion of linoleic acid into compounds that can repress the immune system of the animal. Linolenic acid is also converted into a variety of prostaglandins which control the dividing and multiplying of cells and other cellular functions. Flaxseed, however, may contain other compounds which affect immunity and fertility but may be unknown at this time.

The edible ground flaxseed composition, useful in the present invention, can be a freshly ground raw flaxseed composition of flaxseed which has been ground earlier and has not become toxic, as described herein and in my copending U.S. patent application Ser. No. 07/629,036, now U.S. Pat. No. 5,069,903, or it can be an especially stabilized composition as described in U.S. Pat. No. 4,857,326 or it can be ground raw flaxseed or ground roasted flaxseed. Use of the freshly ground raw flaxseed composition is especially preferred. The disclosures of my copending U.S. patent application Ser. No. 07/629,036 and of U.S. Pat. No. 4,857,326 are expressly incorporated herein by reference.

Further, the flaxseed composition can be in a dry form or in the form of an emulsion or suspension, also as described in my copending U.S. patent application Ser. No. 07/629,036, now U.S. Pat. No. 5,069,903 and U.S. Pat. No. 4,857,326.

More specifically, a first flaxseed composition useful in the present invention is disclosed in my copending U.S. patent application Ser. No. 07/629,036 and is a stable dry edible flaxseed composition comprising ground raw flaxseed. Grinding is necessary so that the linolenic acid is made available to the body in the digestive system. The flaxseed in this composition is ground to a size of from about 1/10 inch to about 1/1000 inch in diameter. A diameter of about 1/10 to 1/100 inch is preferred, and a diameter of about 1/50 to 1/100 is especially preferred.

Any method can be used to grind the flaxseed as long as the temperature is maintained at about 160° F to just above freezing in order to prevent oxidation of the linolenic acid. Particularly suitable methods of grinding the flaxseed can readily be determined by those skilled in the art and include the use of grinders such as a hammermill, impact grinder or Alpine ® grinder (manufactured by Alpine American Corporation, Nadick, Mass.).

In a further embodiment the ground flaxseed is fortified with zinc and/or vitamin B-6.

If the ground flaxseed is to be fortified with zinc and/or vitamin B-6, the zinc and/or vitamin B-6 is simply added to the round flaxseed and thoroughly mixed.

Preferred storage conditions for the flaxseed are from about −25° to about 50°, more preferably from about −10° C. to about 40° C., most preferably from about −5° C. to 30° C.

A second flaxseed composition useful in the present invention is a stable dry edible flaxseed composition prepared as described in U.S. Pat. No. 4,857,326. This stable dry composition of flaxseed is especially high in available Omega-3, and the Omega-3 has a longer shelf-life before becoming rancid as compared to the Omega-3 in other dry compositions containing ground raw flaxseed.

As used herein, the term "Omega-3" refers to three compounds: alpha-linolenic acid (ALNA), and its biologically active metabolic products found only in animal products, docosohexenoic acid (DHA) and eicosopentenoic acid (EPA).

The method for producing this stable dry composition of flaxseed comprises grinding the flaxseed in the presence of vitamin B-6 and zinc ion at a temperature of about 160° F. to just above freezing.

The flaxseed is ground until the ground flaxseed has a size of about 1/10 inch to about 1/1000 inch in diameter. A diameter of about 1/10 to about 1/100 is preferred and a diameter of about 2 1/50 to about 1/100 is especially preferred.

Further details concerning the method of preparing and storing this dry edible ground flaxseed composition can be found by reference to U.S. Pat. No. 4,857,326.

The stable dry edible flaxseed composition described above can be used to produce a third form of flaxseed suitable for use in the present invention, comprising a stable emulsion or suspension of flaxseed.

The stable emulsion or suspension of flaxseed is produced by a specific process that results in an emulsion or suspension of flaxseed which remains chemically stable, i.e. does not turn rancid, and physically stable, i.e. does not separate into components for long periods of time.

The method for producing the stable emulsion or suspension of flaxseed comprises:

(1) grinding the flaxseed in the presence of vitamin B-6 and zinc ion at a temperature of about 160° F to just above freezing;

(2) soaking the flaxseed in an aqueous solution for about 10 minutes to overnight at a temperature of about 160° F. to just above freezing; and (3) blending or homogenizing the soaked, ground flaxseed, with or without further additives, to form a stable emulsion or suspension;

provided that the steps (1) and (2) can be conducted in any order.

Thus, the method for producing a stable emulsion or suspension of flaxseed involves three steps, the first two of which can be conducted in either order. Then the third step is performed.

If the grinding step is conducted first, i.e., before any aqueous solution is present, the grinding is conducted in the same manner as the above-described method for producing a stable dry composition of flaxseed.

If, on the other hand, the grinding step is conducted after the soaking step, the above-described conditions for the method for producing the stable dry composition apply, except that the grinding can also be carried out in an apparatus that is suitable for grinding wet flaxseed, such as a blender. However, as with grinding dry flaxseed, a hammermill, impact grinder, or Alpine Grinder ® can also be used to grind the wet flaxseed.

In either case, the grinding is carried out until the ground flaxseed has a size of about 1/10 inch to about 1/1000 inch diameter, preferably about 1/10 inch to about 1/100 inch diameter, especially preferably about 1/50 inch to about 1/100 inch diameter.

For making the emulsion, the flaxseed is used in an amount of from about 1 to 25 parts by weight per 100 parts by weight of the aqueous solution used in step (2), preferably from about 3 to 20 parts by weight per 100 parts by weight of the aqueous solution used in step (2), and more preferably from about 6 to 12 parts by weight per 100 parts by weight of the aqueous solution used in step (2).

For conducting the soaking step, the solution in which the flaxseed is soaked can be any aqueous solution. Suitable solutions include water and milk. Water is especially preferred.

Further details concerning the method of preparing and storing this flaxseed composition or emulsion can be found by reference to U.S. Pat. No. 4,857,326.

A fourth flaxseed composition useful in the present invention is prepared by roasting whole flaxseed at a temperature of 160° F to 250° F for a time of 10 to 20 minutes depending on batch size and thickness of the layer of material being roasted. The product should not be burned.

The flaxseed can also be lightly roasted before grinding to kill off any undesirable bacteria and to drive off undesirable flavors or other compounds.

The grinding is carried out by the methods disclosed above until the flaxseed has a size of from about 1/10 inch to about 1/1000 inch in diameter. A diameter of about 1/10 to about 1/100 inch is preferred, and a diameter of about 1/50 to about 1/100 is especially preferred.

The flaxseed compositions are administered orally, either by themselves or, more preferably, the dry compositions are mixed with suitable animal feed that contains balanced levels of all essential nutrients.

When the dry flaxseed composition is blended into a conventional animal feed, the biologically effective amount of the flaxseed composition is best expressed in terms of the weight of flaxseed composition per 100 parts by weight of the animal feed fed to the animals in amounts and at intervals commensurate with their normal feeding habits. When expressed in this manner, the biologically effective amounts are the same for all animals and are from about 1 part to about 15 parts by weight of flaxseed composition to about 100 parts by weight of animal feed, more preferably from about 1 part to about 10 parts by weight of flaxseed composition to about 100 parts by weight of animal feed and most preferably from about 2 parts to about 7 parts by weight of flaxseed composition to about 100 parts by weight of animal feed.

In a further embodiment, the animal feed blend further comprises zinc, vitamin B-6 or both zinc and vitamin B-6.

Also, by reference to the above, one skilled in the art can readily determine the effective amount of the composition alone, either dry or in a suspension or emulsion, for each animal. As an example, it has been found that using as little as 3% by weight of total feed of ground flaxseed in the diet of swine is sufficient to increase the average number of live births. Further, using as little as 60g of flaxseed per day per female swine body weight or as little as 1 g of flaxseed per kilogram of female swine body weight can increase the average number of live births. Feeding higher levels for longer period of time and through successive generations can cause larger increases in litter size, up to about 15%, (dry weight basis) of flax in the diet Levels above 15% cause excessively loose stools.

The most preferred method of administering the flaxseed is to begin providing nutrients to the female animal through the uterus by feeding the female animal's mother the flaxseed composition beginning at least during the time of breeding and more preferably one month before breeding, and to continue feeding the bred animal the flaxseed composition all during the mother's pregnancy and through lactation. The mother is fed the flaxseed composition until the weaning of the female offspring on feed containing the flaxseed preparation. The female offspring are then fed feed containing the flaxseed from birth until delivery of their litter.

In another preferred embodiment of administering the flaxseed, nutrients are provided to the female animal through the uterus by feeding the female animal's mother the flaxseed composition beginning one month before the birth of the female animal and to continue feeding the mother during the remainder of the pregnancy and throughout lactation until the birth of the female animal. The mother is fed the flaxseed composition until the weaning of the female offspring on feed containing the flaxseed preparation. The female offspring are then fed feed containing the flaxseed from birth until delivery of their litter.

In another preferred embodiment of administering the flaxseed, nutrients are provided to the female animal at the time of breeding and the female animal is fed the flaxseed throughout 14 the female animal's pregnancy and during the period of lactation.

The method according to the present invention is especially useful for increasing the number of live births in swine and other monogastric animals.

The method is especially effective for female swine. In this embodiment, the ground flaxseed is combined with conventional feed. This feed is typically a mixture of animal and vegetable and grain products and vitamins and minerals. When the ground flaxseed composition is fed to a female swine beginning at least one month before the expected delivery time, the live weaned pig average per sow will increase by 0.5 to 1 pig per litter, because fewer pigs are still born and their immune system is stronger so that more pigs survive from birth to the weaning stage.

When the ground flaxseed composition is fed to the female animal beginning with feeding the female animal's mother during her pregnancy beginning at least one month before the expected delivery time of the female animal, a still further increase in the number of live births results. Thus, if maintained on a diet including flaxseed, the increase in number of live births increases with each subsequent litter.

As an example, when the flaxseed composition was fed to female swine, whose mother had been fed the flaxseed preparation, and then fed to the female swine from its birth through multiple litters, the number of live births was increased from about 8 to about 12 during their first parity and from about 12 to about 17 during subsequent parities.

The present invention also provides an animal feed blend comprising: (1) animal feed, and (2) the above-described stable, dry edible flaxseed composition comprising ground raw flaxseed.

The animal feed blend is produced by mixing the above-described stable, dry, edible flaxseed composition comprising ground raw flaxseed with conventional animal feed as described above and is fed to the animals in amounts and at intervals commensurate with their normal feeding habits as described above.

In a preferred embodiment, the animal feed blend contains ground raw flaxseed fortified with vitamin B-6 and/or zinc.

The invention will now be described by reference to specific examples which, however, are not intended to be limiting.

EXAMPLES

Farmer "S" fed his eight pregnant sows ground flaxseed at the rate of 50 pounds per ton of complete feed during the last month of his sow's pregnancy. His sows produced only one mummified pig, whereas he would normally find 5 to 8 mummified pigs among the 8 litters of piglets. The live weaned litter size increased from 8.5 in the control to 9.4 in the group that was fed flaxseed.

Farmer "V" fed purebred Yorkshire sows ground flaxseed at the rate of 80 pounds per ton of complete feed during the last trimester of their pregnancy. He found no mummified pigs, and his weaned live average increased from 8.5 to 120 piglets per litter. The only change was adding the ground flaxseed to the diet.

Farmer "bH" fed female swine a ground composition of flaxseed in the amount of 150 pounds per ton of complete feed for two generations. The first generation was fed a minimum of 1 month prior to parturition and throughout lactation. Subsequently, the female offspring was fed the flaxseed preparation throughout her lifecycle starting at birth ad throughout breeding and gestation. When this scenario was followed, 50% larger litters were noted as compared with the control group that was fed no flaxseed. Average litter size was 16.25 in the groups fed flaxseed. The control group averaged 10.5 pigs per litter. No disease outbreaks were noted.

Farmer "L" fed 12 gilts flaxseed in the amount of 80 pounds per ton of complete feed, from the time of weaning through gestation to parturition. The gilts averaged 12.5 live births compared to 8.5 live births for the control group of gilts not fed a flaxseed composition. All other conditions were kept identical. At birth, the pigs had a strong immune system as evidenced by the fact that they and did not suffer from any infectious diseases even though they were exposed to rhinitis and other diseases.

Farmer "P" fed a gilt a flaxseed composition from the time of breeding until delivery and through lactation. He took three gilts from her litter and fed them flaxseed until they farrowed. They averaged 12.2 pigs per litter. Farmer "P" then took 6 gilts from these three litters and fed them flaxseed all their life. The farmer then bred these gilts at 4½ months of age. At 8½ months of age these gilts averaged 8.2 piglets per litter. Normally gilts are not bred until they are 7 to 9 months of age. The piglets were born in a contaminated pen but did not succumb to any diseases.

While the invention has been described in detail and with reference to specific embodiments thereof, it will be apparent to one skilled in the art that various changes and modifications can be made therein without departing from the spirit and scope thereof.

What is claimed is:

1. A method for increasing the number of live births to a female animal, comprising administering orally to said female animal beginning at least one week before the expected time of birth of said female animal's offspring and continuing at least until the birth of said offspring, a biologically effective amount of an edible composition comprising ground flaxseed.

2. The method of claim 1, wherein said composition further comprises zinc, or vitamin B-6, or both zinc and vitamin B-6.

3. The method of claim 2, wherein said composition comprises ground raw flaxseed.

4. The method of claim 3, wherein said composition is administered in a mixture with an animal feed.

5. The method of claim 4, wherein said administering to said female animal continues through lactation.

6. The method of claim 4, wherein said administering to said female animal begins at the time of breeding and continues until the birth of said female animal's offspring.

7. The method of claim 4, wherein said biologically effective amount is from about 1 part to about 15 parts by weight of said composition to about 100 parts by weight of animal feed.

8. The method of claim 4, wherein said biologically effective amount is from about 1 part to about 10 parts by weight of said composition to about 100 parts by weight of animal feed.

9. The method of claim 4, wherein said biologically effective amount is from about 2 parts to about 7 parts by weight of said composition to about 100 parts by weight of animal feed.

10. The method of claim 4, wherein said female animal is monogastric.

11. The method of claim 4, wherein, said female animal is a female swine.

12. The method of claim 1, wherein said composition comprises ground raw flaxseed.

13. The method of claim 12, wherein said composition is administered in a mixture with an animal feed.

14. The method of claim 13, wherein said administering to said female animal continues through lactation.

15. The method of claim 13, wherein said administering to said female animal begins at the time of breeding and continues until the birth of said female animal's offspring.

16. The method of claim 13, wherein said biologically effective amount is from about 1 part to about 15 parts by weight of said composition to about 100 parts by weight of animal feed.

17. The method of claim 13, wherein said biologically effective amount is from about 1 part to about 10 parts by weight of said composition to about 100 parts by weight of animal feed.

18. The method of claim 13, wherein said biologically effective amount is from about 2 parts to about 7 parts by weight of said composition to about 100 parts by weight of animal feed.

19. The method of claim 13, wherein said female animal is monogastric.

20. The method of claim 13, wherein said female animal is a female swine.

21. The method of claim 3, wherein said administering to said female animal continues through lactation.

22. The method of claim 3, wherein said administering to said female animal begins at the time of breeding and continues until the birth of said female animal's offspring.

23. The method of claim 3, wherein said female animal is monogastric.

24. The method of claim 3, wherein said female animal is a female swine.

25. The method of claim 12, wherein said administering to said female animal continues through lactation.

26. The method of claim 12, wherein said administering to said female animal begins at the time of breeding and continues until the birth of said female animal's offspring.

27. The method of claim 12, wherein said female animal is monogastric.

28. The method of claim 12, wherein said female animal is a female swine.

29. The method of claim 2, wherein said administering to said female animal continues through lactation.

30. The method of claim 2, wherein said administering to said female animal begins at the time of breeding and continues until the birth of said female animal's offspring.

31. The method of claim 2, wherein said female animal is monogastric.

32. The method of claim 2, wherein said female animal is a female swine.

33. The method of claim 1, wherein said administering to said female animal continues through lactation.

34. The method of claim 1, wherein said administering to said female animal begins at the time of breeding and continues until the birth of said female animal's offspring.

35. The method of claim 1, wherein said female animal is monogastric.

36. The method of claim 1, wherein said female animal is a female swine.

37. A method for increasing the number of live births to a female animal, comprising administering orally to said female animal beginning by feeding said female animal's mother at least one month before breeding and continuing through the weaning of said female animal, and then feeding said female animal from weaning until the birth of one or more litters to the female animal, a biologically effective amount of an edible composition comprising ground flaxseed.

38. The method of claim 37, wherein said composition further comprises zinc, an vitamin B-6, or both zinc and vitamin B-6.

39. The method of claim 38, wherein said composition comprises ground raw flaxseed.

40. The method of claim 39, wherein said composition is administered in a mixture with an animal feed.

41. The method of claim 40, wherein said administering to said female animal begins by feeding said female animal's mother at least during the time of breeding of said female animal's mother and continues through the weaning of said female animal, and then feeding said female animal from weaning until the birth of one or more litters to the female animal, a biologically effective amount of an edible composition comprising ground flaxseed.

42. The method of claim 37, wherein said composition comprises ground raw flaxseed.

43. The method of claim 42, wherein said composition is administered in a mixture with an animal feed.

44. The method of claim 43, wherein said administering to said female animal begins by feeding said female animal's mother at least during the time of breeding of said female animal's mother and continues through the weaning of said female animal, and then feeding said female animal from weaning until the birth of one or more litters to the female animal, a biologically effective amount of an edible composition comprising ground flaxseed.

45. The method of claim 37, wherein said administering to said female animal begins by feeding said female animal's mother at least during the time of breeding of said female animal's mother and continues through the weaning of said female animal, and then feeding said female animal from weaning until the birth of one or more litters to the female animal, a biologically effective amount of an edible composition comprising ground flaxseed.

46. The method of claim 40, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

47. The method of claim 40, wherein said administering continues through more than one litter of said female animal.

48. The method of claim 43, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

49. The method of claim 43, wherein said administering continues through more than one litter of said female animal.

50. The method of claim 39, wherein said administering to said female animal begins by feeding said female animal's mother at least during the time of breeding of said female animal's mother and continues through the weaning of said female animal, and then feeding said female animal from weaning until the birth of one or more litters to the female animal, a biologically effective amount of an edible composition comprising ground flaxseed.

51. The method of claim 39, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

52. The method of claim 39, wherein said administering continues through more than one litter of said female animal.

53. The method of claim 42, wherein said administering to said female animal begins by feeding said female animal's mother at least during the time of breeding of said female animal's mother and continues through the weaning of said female animal, and then feeding said female animal from weaning until the birth of one or more liters to the female animal, a biologically effective amount of an edible composition comprising ground flaxseed.

54. The method of claim 42, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

55. The method of claim 42, wherein said administering continues through more than one litter of said female animal.

56. The method of claim 38, wherein said administering to said female animal begins by feeding said female animal's mother at least during the time of breeding of said female animal's mother and continues through the weaning of said female animal, and then feeding said female animal from weaning until the birth of one or more litters to the female animal, a biologically effective amount of an edible composition comprising ground flaxseed.

57. The method of claim 38, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

58. The method of claim 38, wherein said administering continues through more than one litter of said female animal.

59. The method of claim 37, wherein said administering to said female animal begins by feeding said female animal's mother at least one month prior to the time of birth of said female animal and continues through the weaning of said female animal, and then feeding said female animal from weaning until the birth of one or more litters to the female animal, a biologically effective amount of an edible composition comprising ground flaxseed.

60. The method of claim 37, wherein said administering continues through more than one litter of said female animal.

61. An animal feed blend comprising: (1) animal feed and (2) a stable dry edible flaxseed composition comprising ground raw flaxseed.

* * * * *